United States Patent
Furuta et al.

(10) Patent No.: US 9,448,194 B2
(45) Date of Patent: Sep. 20, 2016

(54) APPARATUS AND METHOD OF DETERMINING FAILURE IN THERMOSTAT

(71) Applicant: MITSUBISHI JIDOSHA KOGYO KABUSHIKI KAISHA, Tokyo (JP)

(72) Inventors: Katsuhiro Furuta, Tokyo (JP); Kenji Saito, Tokyo (JP); Hitoshi Kamura, Tokyo (JP)

(73) Assignee: MITSUBISHI JIDOSHA KOGYO KABUSHIKI KAISHA, Tokyo (JP)

( * ) Notice: Subject to any disclaimer, the term of this patent is extended or adjusted under 35 U.S.C. 154(b) by 538 days.

(21) Appl. No.: 13/912,496

(22) Filed: Jun. 7, 2013

(65) Prior Publication Data
US 2014/0023107 A1  Jan. 23, 2014

(30) Foreign Application Priority Data
Jul. 23, 2012 (JP) .................................. 2012-162937

(51) Int. Cl.
*G01N 25/72* (2006.01)
*G01M 15/00* (2006.01)
*F01P 11/16* (2006.01)

(52) U.S. Cl.
CPC ............ *G01N 25/72* (2013.01); *F01P 11/16* (2013.01); *F01P 2025/32* (2013.01); *F01P 2060/08* (2013.01)

(58) Field of Classification Search
USPC ................... 374/144, 145, 57; 701/114, 112; 73/114.68, 114.01
See application file for complete search history.

(56) References Cited

U.S. PATENT DOCUMENTS 6,529,818 B2   3/2003 Kitajima et al.
6,615,647 B2 * 9/2003 Niki .................. F01P 11/16
                                                73/114.68

(Continued)

FOREIGN PATENT DOCUMENTS

CN    102482985 A    5/2012
JP    4661767 B2     3/2011

OTHER PUBLICATIONS

Chinese Office Action mailed May 28, 2015 in corresponding Chinese Application No. 201310308282.7 with an English translation.

(Continued)

*Primary Examiner* — Lisa Caputo
*Assistant Examiner* — Nasir U Ahmed
(74) *Attorney, Agent, or Firm* — Birch, Stewart, Kolasch & Birch, LLP

(57) ABSTRACT

An apparatus for determining a failure in a thermostat for controlling the flow of a coolant into a radiator in response to an actual water temperature of the coolant for an engine in a vehicle includes: a water temperature detector that detects the actual water temperature; a water temperature estimator that calculates an estimated water temperature of the coolant; and a failure determining unit that compares the actual water temperature detected by the water temperature detector with the estimated water temperature calculated by the water temperature estimator under cold start of the engine and determines whether the thermostat is valve-open failure. In an engine nonoperating mode including at least automatic stop of the engine, the water temperature estimator applies a behavior of the actual water temperature to an estimated water temperature calculated immediately before automatic stop of the engine to calculate an estimated water temperature in the engine nonoperating mode.

10 Claims, 6 Drawing Sheets

(56) References Cited

U.S. PATENT DOCUMENTS

| | | | |
|---|---|---|---|
| 8,303,174 B2 * | 11/2012 | Kasahara | F01N 3/2066 374/1 |
| 8,770,834 B2 | 7/2014 | Suzuki | |
| 2001/0005807 A1 * | 6/2001 | Kitajima | F02N 11/0803 701/112 |
| 2002/0088274 A1 | 7/2002 | Oka et al. | |
| 2002/0193936 A1 * | 12/2002 | Saito | F02M 25/0809 701/114 |
| 2004/0168510 A1 * | 9/2004 | Wakahara | F01P 11/16 73/114.71 |
| 2012/0106590 A1 | 5/2012 | Suzuki | |

OTHER PUBLICATIONS

Chinese Office Action mailed Jan. 18, 2016 in corresponding Chinese Application No. 201310308282.7 with an English translation.

* cited by examiner

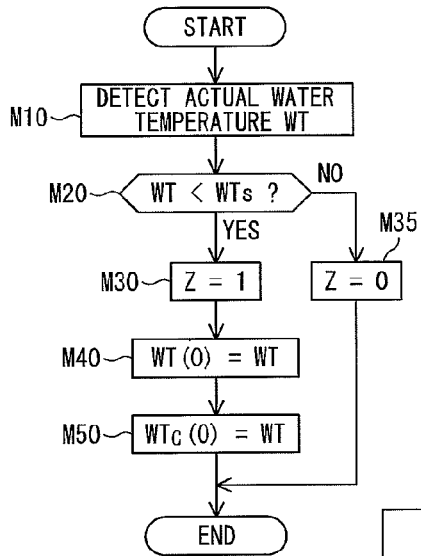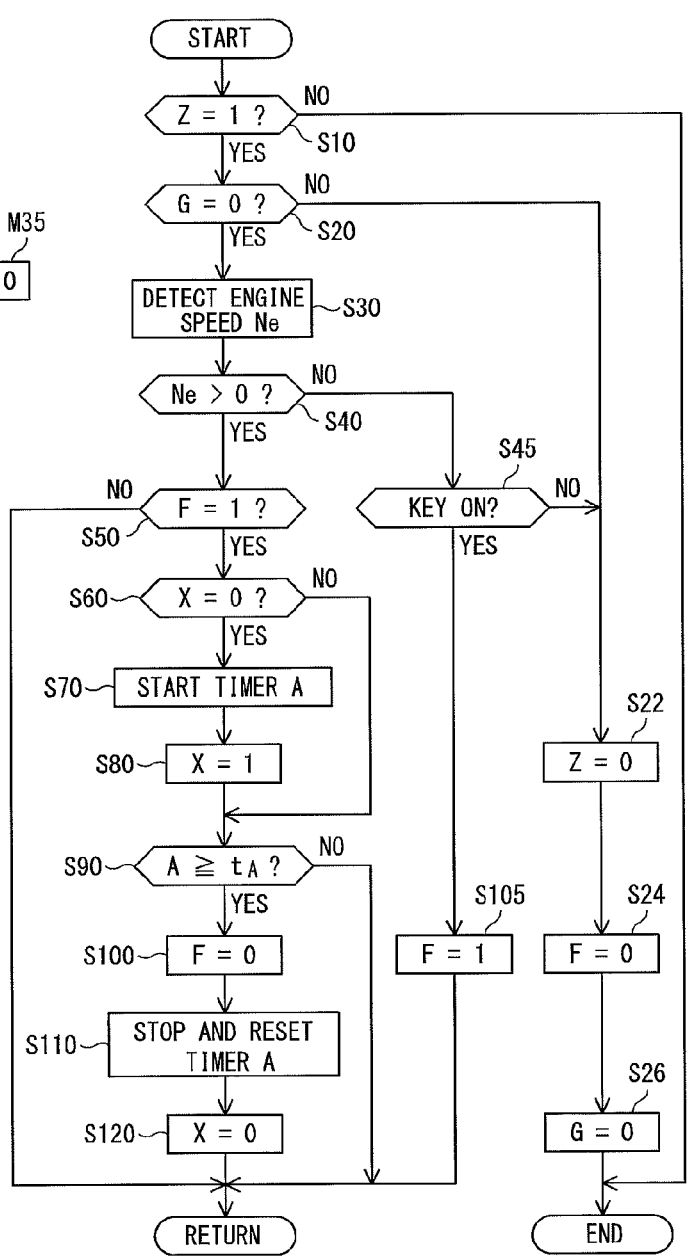

APPARATUS AND METHOD OF DETERMINING FAILURE IN THERMOSTAT

CROSS-REFERENCE TO THE RELATED APPLICATION

This application incorporates by references the subject matter of Application No. 2012-162937 filed in Japan on Jul. 23, 2012 on which a priority claim is based under 35 U.S.C. §119(a).

FIELD

The present invention relates to an apparatus and a method of determining a valve-open failure in a thermostat provided in a cooling system of an engine.

BACKGROUND

A radiator and a thermostat are disposed in a cooling channel through which a coolant for an engine circulates. If the temperature of the coolant is equal to or higher than a predetermined temperature, the thermostat opens a valve to circulate the coolant through the radiator to dissipate heat; otherwise, if the temperature of the coolant is lower than the predetermined temperature, the thermostat closes the valve to prevent the coolant from circulating through the radiator (i.e., causes the coolant to bypass the radiator), thereby raising the temperature.

In the event of a valve-open failure (i.e., a failure of the valve being fixed in an open state) in the thermostat provided in such an engine cooling system, even a coolant at a temperature under the predetermined temperature also circulates the radiator. This hinders a quick increase in the coolant temperature to cause time-consuming warm-up of the engine, resulting in poor fuel economy and an increase in emission.

Techniques for determining a valve-open failure in a thermostat have accordingly been proposed. For example, an apparatus described in Patent Literature 1 (Japanese Patent No. 4661767) compares an estimated temperature of a coolant for an engine and a detected temperature with a reference temperature to determine the operational state of the thermostat. The apparatus also cancels the determined results during a vehicle operation condition that may cause a wrong determination, in order to increase the accuracy of determination.

The temperature of a coolant for an engine, which may be estimated from the amounts of heat absorbed and heat dissipated by the coolant, needs to be estimated by arithmetic operations different between the engine operating mode and the engine stop mode since heat-absorption and heat-dissipation by the coolant are different between these two modes. Nevertheless, estimation by the arithmetic expressions different between the engine operating mode and the engine stop mode leads to an increase in an operation load. A single arithmetic expression for different operation modes, however, lowers the accuracy of estimating the temperature of the coolant in the case requiring different arithmetic expressions.

In addition, a vehicle having the function of brief stopping without idling experiences a longer engine-stop time (including the time period of the engine being automatically stopped) than that of a vehicle without this function. For this reason, a single arithmetic expression for both the engine operating mode and the engine stop mode may lead to reduced estimation accuracy of the temperature of the coolant, resulting in an erroneous decision in a determination of a thermostat failure. Furthermore, vehicles that can run while their engines being automatically stopped for a long time, such as plug-in hybrid electric vehicles (PHEVs), have been put into practical use recently, which might increase erroneous decision cases in a failure determination.

The apparatus disclosed in Patent Literature 1 cancels the results of a failure determination determined within a time period from a brief stop without idling to a lapse of a predetermined time from the restart of the engine because this period for a vehicle tends to cause an erroneous decision. Such cancelling, notwithstanding, gives no results on the normality of the thermostat and requires another failure determination to acquire accurate results, which, unfortunately, hinders immediate determination of the operational state of the thermostat. In particular, a vehicle capable of running while its engine being automatically stopped for a long while disadvantageously leads to significantly lower accuracy of estimating a coolant temperature, which phenomenon needs a longer predetermined time after engine restarts to prevent an erroneous determination. As a result, cancelling of the determined results increases. Consequently, acquiring determined results takes a long time.

SUMMARY

Technical Problems

An object of the subject matter, which has been invented in view of such circumstances, is to provide a simple apparatus and method of determining a failure in a thermostat which ensure the accurate estimation of the temperature of a coolant during the automatic stopping of an engine and allow for a high-accuracy determination of the failure.

Solution to Problems (1) An apparatus of determining a failure in a thermostat disclosed herein is an apparatus of determining a failure in a thermostat for controlling the flow of a coolant into a radiator in response to an actual water temperature of the coolant for an engine in a vehicle, in which the apparatus includes a water temperature detector that detects the actual water temperature; a water temperature estimator that calculates an estimated water temperature of the coolant; and a failure determining unit that compares the actual water temperature detected by the water temperature detector with the estimated water temperature calculated by the water temperature estimator under cold start of the engine and determines whether the thermostat is valve-open failure. In an engine nonoperating mode including at least automatic stop of the engine, the water temperature estimator applies a behavior of the actual water temperature to an estimated water temperature calculated immediately before automatic stop of the engine to calculate an estimated water temperature in the engine nonoperating mode.

(2) Preferably, in the engine nonoperating mode, the water temperature estimator calculates the estimated water temperature assumed to vary, with a temperature gradient identical to a temperature gradient of the actual water temperature. That is, in the engine nonoperating mode, the water temperature estimator preferably calculates the estimated water temperature assumed to vary, with the same temperature gradient as that of the actual water temperature, from a starting temperature which is the estimated water temperature calculated immediately before the automatic stop of the engine.

(3) Preferably, the apparatus further includes a mode determiner that determines whether the vehicle is in the engine nonoperating mode. In this case, the mode determiner preferably determines a period between restart of the automatically stopped engine and a lapse of a predetermined time to be the engine nonoperating mode. That is, after cold start of the engine, the mode determiner preferably determines the engine nonoperating mode to be in the time period between the automatic stop of the engine due to, for example, brief stop without idling and a lapse of the predetermined time from the restart of the engine.

(4) More preferably, the mode determiner revises the predetermined time in response to a variation in the actual water temperature in the automatically stopped engine. The mode determiner may also revise the predetermined time in response to the time of the automatic stop of the engine (stop time), instead of a variation in the actual water temperature in the automatically stopped engine. This is because a longer automatic stop time increases the variation in the actual water temperature and a shorter automatic stop time reduces the variation in the actual water temperature, that is, the variation in the actual water temperature in the automatically stopped engine is correlative to the stop time.

(5) Preferably, the failure determining unit stops comparison between the actual water temperature and the estimated water temperature in the engine nonoperating mode and restarts the comparison at the termination of the engine nonoperating mode.

(6) More preferably, in this case, at the termination of the engine nonoperating mode, the water temperature estimator adds a variation in the actual water temperature during a period between a time immediately before the automatic stop and the termination to the estimated water temperature calculated immediately before the automatic stop.

(7) A method of determining a failure in a thermostat disclosed herein is a method of diagnosing a failure in a thermostat for controlling the flow of a coolant into a radiator in response to an actual water temperature of the coolant for an engine in a vehicle, in which the method includes determining whether the engine is cold-started; detecting the actual water temperature, if the engine is cold-started, and applying a behavior of the actual water temperature to an estimated water temperature calculated immediately before automatic stop of the engine in an engine nonoperating mode including at least automatic stop of the engine to calculate an estimated water temperature in the engine nonoperating mode; and comparing the actual water temperature with the estimated water temperature to determine whether the thermostat is valve-open failure.

Advantageous Effects

The apparatus of determining a failure in a thermostat disclosed herein compares the actual water temperature of a coolant with the estimated temperature of the coolant. In the engine nonoperating mode including at least automatic stop of the engine, the apparatus applies the behavior of the actual water temperature to the estimated water temperature calculated immediately before the automatic stop of the engine to calculate the estimated water temperature in the engine nonoperating mode. This can prevent a reduction in estimation accuracy of the estimated water temperature during the automatic stop of the engine. That is, in the engine nonoperating mode, the estimated water temperature determined from the behavior of the actual water temperature does not involve a significant deviation from the actual variation in the coolant (i.e., change in the actual water temperature), which can ensure the accuracy of estimating the temperature of the coolant even during the automatic stop of the engine.

Accordingly, a failure in the thermostat can be determined using the high-accuracy estimated water temperature, which can lead to an improvement in the accuracy of the failure determination. In addition, an operation load can be suppressed with the simple configuration that only applies the behavior of the actual water temperature to the estimated water temperature calculated immediately before the automatic stop.

Similarly, in the engine nonoperating mode including at least automatic stop of the engine, a method of determining a failure in thermostat disclosed herein applies the behavior of the actual water temperature to the estimated water temperature calculated immediately before the automatic stop of the engine to calculate the estimated water temperature in the engine nonoperating mode and compares this estimated water temperature with the actual water temperature to determine a valve-open failure in the thermostat. This can prevent a reduction in estimation accuracy of the estimated water temperature during the automatic stop of the engine and ensure the accuracy of estimating the temperature of the coolant even during the automatic stop of the engine. Accordingly, a failure in the thermostat can be determined using the high-accuracy estimated water temperature, which can lead to an improvement in the accuracy of the failure determination. In addition, an operation load can be suppressed and a failure determination can be facilitated due to the simple configuration that only applies the behavior of the actual water temperature to the estimated water temperature calculated immediately before the automatic stop.

BRIEF DESCRIPTION OF DRAWINGS

The nature of this invention, as well as other objects and advantages thereof, will be explained in the following with reference to the accompanying drawings, in which like reference characters designate the same or similar parts throughout the figures and wherein:

FIG. 2A illustrates the engine speed; FIG. 2B illustrates an operational mode; FIG. 2C illustrates the temperature of a coolant; and FIG. 2D illustrates a temporal change in a counter for failure determination;

FIG. 3A illustrates the engine speed; FIG. 3B illustrates an operational mode; FIG. 3C illustrates the temperature of a coolant; and FIG. 3D illustrates a temporal change in a counter for failure determination;

FIGS. 4A and 4B are flow charts illustrating processes executed by a mode determiner: FIG. 4A illustrates a flow chart of determining engine start; and FIG. 4B illustrates a flow chart of determining a normal running mode or an engine nonoperating mode;

DESCRIPTION OF EMBODIMENTS

An embodiment will now be described with reference to the drawings. It is noted that the embodiment described below is only an example and should not be intended to exclude the application of various modifications and techniques that are not illustrated in the embodiment. A plug-in hybrid electric vehicle (PHEV), which operates using an engine and a motor, is herein illustrated as an example.

[1. Configuration of Apparatus]

Figure 1:
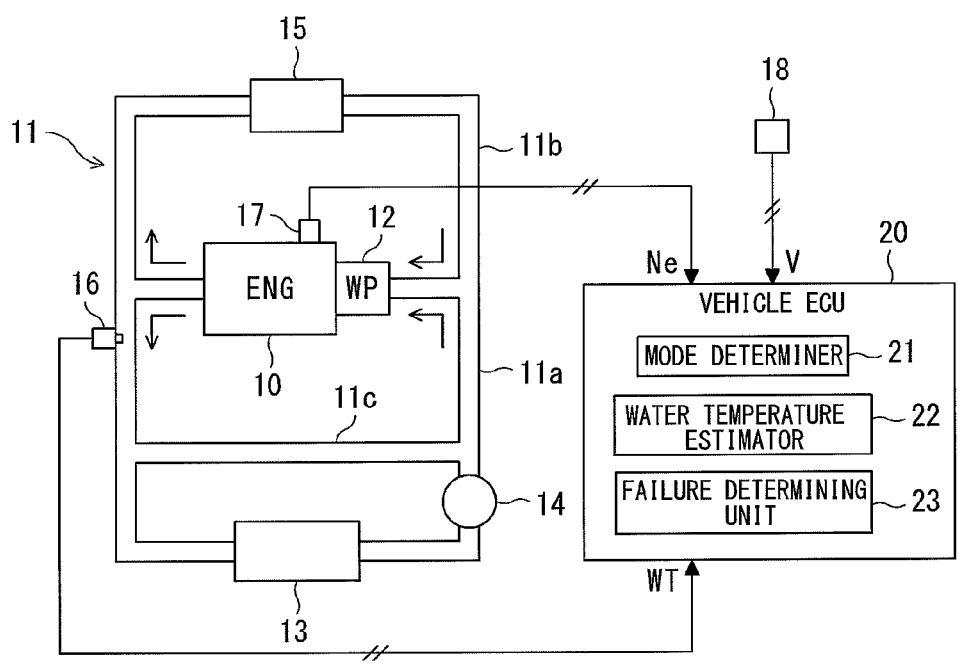
FIG. 1 is a block diagram illustrating an apparatus of determining a failure in a thermostat according to an embodiment and engine cooling channels provided with the apparatus.

FIG. 1 illustrates a cooling channel 11 for an engine 10 provided with an apparatus of determining a failure according to the present embodiment. The cooling channel 11 is a passage for the circulation of a coolant flowing in a water jacket (not shown) of the engine 10. The cooling channel 11 extends from the water jacket, branches into a first circulation channel 11a and a second circulation channel 11b, which join upstream of a water pump (WP) 12, and returns to the water jacket of the engine 10.

The water pump 12 is a mechanical pump for circulating the coolant by means of the power of the engine 10. The volume Q of the coolant discharged from the water pump 12 is proportional to the engine speed Ne. Thus, for example, when the engine 10 is automatically stopped in response to the switching of the operating power for the vehicle from the engine to the motor, the water pump 12 is also stopped, which discontinues the circulation of the coolant. The engine 10 is also automatically stopped when the vehicle briefly stops without idling at a red light, for example; the water pump 12 is accordingly stopped, which also discontinues the circulation of the coolant. Such a case where the engine 10 is automatically stopped will be hereinafter referred to as "automatic stop of the engine 10." That is, the automatic stop of the engine 10 indicates that a computer automatically stops the engine 10 regardless of the intention of a driver.

The first circulation channel 11a has a radiator 13 and a thermostat 14 therein, and the coolant passes through the radiator 13 and is cooled due to heat dissipation. The first circulation channel 11a has a bypass channel 11c that connects an upstream point of the radiator 13 to a downstream point of the thermostat 14 and bypasses the radiator 13 and the thermostat 14.

The thermostat 14 is a valve mechanism that opens and closes in response to the temperature of the coolant (actual water temperature) WT, thereby controlling the flow of the coolant into the radiator 13. If the actual water temperature WT is low, the thermostat 14 closes the valve to flow the coolant through the bypass channel 11c; in contrast, if the actual water temperature WT is high, the thermostat 14 opens the valve to allow the coolant to flow into the radiator 13. That is, if the actual water temperature WT is low, the thermostat 14 causes the coolant to bypass the radiator 13, thereby quickly warming the coolant; in contrast, if the actual water temperature WT is high, the thermostat 14 causes the coolant to pass through the radiator 13, thereby cooling the coolant.

The second circulation channel 11b has a heater 15 therein, which is a part of an air-conditioning apparatus (not shown). The heater 15 absorbs the heat from the coolant generated by cooling the engine 10 and heats up the air using the absorbed heat to warm the passenger compartment. That is, the coolant also dissipates heat while passing through the heater 15.

The cooling channel 11 is provided with a temperature sensor (water temperature detector) 16 for detecting the actual water temperature WT of the coolant. The temperature sensor 16 may be provided at any position such as an upstream point of the first circulation channel 11a as illustrated in FIG. 1 or a point near the water jacket or the water pump 12.

The engine 10 also has an engine speed sensor 17 for detecting the engine speed Ne near a crankshaft (not shown). In addition, the vehicle includes a vehicle speed sensor 18 for detecting the vehicle speed V. The information items on the actual water temperature WT, the engine speed Ne, and the vehicle speed V detected by the temperature sensor 16, the engine speed sensor 17, and the vehicle speed sensor 18, respectively, are sent to a vehicle electric control unit (vehicle ECU) 20 as needed.

The vehicle includes a motor and a battery (both not shown), which is a power source for the motor. The motor is a motor generator having the function of running the vehicle by using the power from the battery and the function of regenerating power by means of regenerative braking or the inertia of the vehicle during the coasting. The vehicle ECU 20 determines the running mode of the vehicle by the engine 10, the motor, or combination thereof.

The vehicle includes the vehicle ECU 20 for entirely controlling the vehicle. The vehicle ECU 20 is a computer including a CPU for executing various arithmetic processes, ROM for storing programs and data needed for the control therein, RAM for temporarily storing arithmetic results from the CPU therein, input and output ports for inputting and outputting signals to and from an external unit, and a timer for measuring the amount of elapsed control time. The inputs of the vehicle ECU 20 are connected to the temperature sensor 16, the engine speed sensor 17, and the vehicle speed sensor 18. The outputs of the vehicle ECU 20 are connected to other ECUs (not shown) such as a battery ECU, an air-conditioning ECU, and a brake ECU. The vehicle ECU 20 controls the engine 10 and the motor on the basis of the information on the remaining battery charge, the vehicle speed, etc.

Among the control menus of the vehicle ECU 20, the control related to a determination of a failure in the thermostat 14 will now be described. The thermostat 14 opens or closes in response to the actual water temperature WT to control the flow of the coolant, as described above. Nevertheless, in the event of a failure of the thermostat 14 being fixed in an open state without closing (hereinafter, the failure is referred to as "valve-open failure"), even a coolant at a low actual water temperature WT passes through the radiator 13, which hinders a quick increase in the temperature, resulting in poor fuel economy and an increase in emission. Thus, the vehicle ECU 20 determines a valve-open failure in the thermostat 14.

[2. Configuration of Control]

The vehicle ECU 20 includes a functional element that is a mode determiner 21 for determining the mode depending on the state of the vehicle, a functional element that is a water temperature estimator 22 for estimating the temperature of a coolant, and a functional element that is a failure determining unit 23 for determining a valve-open failure in the thermostat 14.

After the cold start of the engine 10, the vehicle ECU 20 compares the actual water temperature WT, detected by the temperature sensor 16, with an estimated water temperature $WT_C$ calculated by the water temperature estimator 22 to determine a failure in the thermostat 14. The failure determination is carried out only once between turning-on of an ignition (IG) switch (not shown) (hereinafter, referred to as "the key being brought to the ON position") and turning-off of the IG switch (hereinafter, referred to as "the key being brought to the OFF position"). Note that the estimated water temperature $WT_C$ calculated by the water temperature estimator 22 is a temperature estimated depending on the operational conditions of the engine 10, and the estimated water temperature $WT_C$ is substantially equal to the actual water temperature WT if the thermostat 14 is normal. The present embodiment is particularly characterized by the calculation of the estimated water temperature $WT_C$ and a failure determination, in the engine nonoperating mode including at least the automatic stop of the engine 10.

The mode determiner 21 determines whether the vehicle is in the engine nonoperating mode (engine stop mode) on the basis of the actual water temperature WT detected by the temperature sensor 16 and the engine speed Ne detected by the engine speed sensor 17. The engine nonoperating mode determined by the mode determiner 21 is between the restart of the automatically stopped engine 10 and a lapse of a predetermined time $t_A$. That is, the engine nonoperating mode refers to a mode in a time period after the cold start of the engine 10, between the automatic stop of the engine 10 and a lapse of the predetermined time $t_A$ after the restart of the engine 10. Note that the predetermined time $t_A$ here is a predefined constant value.

The mode determiner 21 determines the cold start condition of the engine 10 only once at the time of the key being brought to the ON position. The mode determiner 21 compares the actual water temperature WT detected by the temperature sensor 16 with a predetermined temperature $WT_S$. If the actual water temperature WT is lower than the predetermined temperature $WT_S$, the mode determiner 21 determines the cold start; otherwise, the mode determiner 21 determines the hot start. The predetermined temperature $WT_S$ is a threshold used for the determination of whether the engine 10 is cold-started or hot-started and is referred to as "start-up determination temperature $WT_S$."

After the determination of the cold start of the engine 10, the mode determiner 21 further determines whether the engine 10 is operating (i.e., in the normal running mode) or the engine is being automatically stopped (i.e., in the engine nonoperating mode) on the basis of the engine speed Ne of the engine 10. The mode determiner 21 determines the engine nonoperating mode in the case of the automatic stop of the engine 10 (i.e., the engine speed Ne being zero) despite the key being still in the ON position. After the restart of the engine 10, the mode determiner 21 determines the engine nonoperating mode during the period between the restart and a lapse of the predetermined time $t_A$ and determines the normal running mode after the lapse of the predetermined time $t_A$.

It is noted that the reason for the determination of the normal running mode or the engine nonoperating mode is to ensure the accuracy of the estimated water temperature $WT_D$ calculated by the water temperature estimator 22. The automatic stop of the engine 10 leads to the stop of the water pump 12, which discontinues the circulation of the coolant through the cooling channel 11. Thus, the same arithmetic method as that used while the engine 10 is operating would give an estimated water temperature $WT_C$ significantly different from the actual water temperature WT, resulting in a decrease in the accuracy of a failure determination.

The reason will now be described why the engine nonoperating mode involves not only the period during the automatic stop of the engine 10 but also the period between the restart of the engine 10 and a lapse of the predetermined time $t_A$. The coolant starts again to circulate through the cooling channel 11 in response to the restart of the engine 10. Immediately after the restart of the engine 10, nevertheless, the instability of heat-absorption and heat-dissipation by the coolant at an area for water temperature estimation may lead to lower estimation accuracy of coolant temperature. The coolant which was in the cooling channel 11 during the automatic stop of the engine 10 has uneven temperatures based on positions. Low- and moderate-temperature portions coexist in the coolant, for example. For this reason, the actual water temperature WT detected by the temperature sensor 16 immediately after the restart of the engine 10 is various, which may lower the accuracy of a failure determination. Thus, after the restart of the automatically stopped engine 10, the temperature sensor 16 waits until the circulation of the coolant through the cooling channel 11 enough to level out the uneven temperatures of the coolant. The wait time is the predetermined time $t_A$. Note that the mode determiner 21 determines the operational mode only once before a failure determination.

The water temperature estimator 22 estimates the temperature of the coolant (i.e., calculates an estimated water temperature $WT_C$) by different methods between the normal running mode and the engine nonoperating mode. In the normal running mode, the water temperature estimator 22 calculates the total amount of heat $Q_T$ based on the received heat (heat-absorption) $Q_A$ by the coolant per unit time and the dissipated heat (heat-dissipation) $Q_C$ from the coolant per unit time and calculates variations in water temperature (the amounts of changes in temperature) $\Delta WT_C$ on the basis of the total amount of heat $Q_T$. The water temperature estimator 22 then accumulates the variations in water temperature $\Delta WT_C$ together to calculate the estimated water temperature $WT_C$. The variation in water temperature $\Delta WT_C$ per unit time corresponds to the gradient (inclination) in temperature. The received heat $Q_A$ and the dissipated heat $Q_C$ by the coolant are calculated based on, for example, the engine speed Ne of the engine 10 and the vehicle speed V.

In the engine nonoperating mode, the water temperature estimator 22 uses an estimated water temperature $WT_C$ calculated immediately before the engine nonoperating mode (i.e., immediately before the automatic stop of the engine 10) as a starting temperature $WT_{C0}$. The water temperature estimator 22 applies the behavior of the actual water temperature WT detected by the temperature sensor 16 to the starting temperature $WT_{C0}$ to calculate an estimated water temperature $WT_C$ in the engine nonoperating mode. That is, the estimated water temperature $WT_C$ in the engine nonoperating mode is assumed to vary from the starting temperature $WT_{C0}$ with the same temperature gradient as that of the actual water temperature WT. This is because the calculation of the estimated water temperature $WT_C$ in the normal running mode as described above cannot be used during the automatic stop of the engine 10; specifically, the arithmetic method for the normal running mode utilizing the received heat $Q_A$ and the dissipated heat $Q_C$ by the coolant leads to a reduction in estimation accuracy in the engine nonoperating mode.

The failure determining unit 23 compares the actual water temperature WT detected by the temperature sensor 16 with the estimated water temperature $WT_C$ calculated by the water temperature estimator 22 to determine the operational state of the thermostat 14. Since the actual water temperature WT of the coolant is low at the cold start of the engine 10, the normal thermostat 14 closes the valve to circulate the coolant without passing through the radiator 13. As a result, the coolant is quickly warmed, so that the actual water temperature WT increases faster than the estimated water temperature $WT_C$. In contrast, if the thermostat 14 is valve-open failure, the coolant is led to the radiator 13 immediately after the cold start of the engine 10. As a result, it takes a long time to warm the coolant, so that the estimated water temperature $WT_C$ increases faster than the actual water temperature WT. The failure determining unit 23 determines the operational state of the thermostat 14 using such a difference in temperature increase.

The failure determining unit 23 determines that the thermostat 14 is "valve-open failure" if all of conditions (1) to (3) below are fulfilled:
(1) The actual water temperature WT is lower than a predetermined temperature $WT_{TH}$;
(2) The estimated water temperature $WT_C$ is equal to or higher than the predetermined temperature $WT_{TH}$; and
(3) The state fulfilling condition (2) continues for a predetermined time $t_B$.

In contrast, the failure determining unit 23 determines that the thermostat 14 is "normal" if condition (4) below is fulfilled:
(4) The actual water temperature WT is equal to or higher than the predetermined temperature $WT_{TH}$.

That is, if condition (1) is not fulfilled regardless of the fulfillment of condition (2), i.e., if condition (4) is fulfilled, the thermostat 14 is determined to be "normal." Note that the predetermined temperature $WT_{TH}$ is a threshold used for the determination of the operational state of the thermostat 14. To determine the fulfillment of condition (3), the failure determining unit 23 starts the measurement by a counter (hereinafter, also referred to as "counter for failure determination") if condition (2) is fulfilled. If the counter value N reaches a predetermined value $N_{TH}$, the failure determining unit 23 determines the fulfillment of condition (3). Note that the predetermined value $N_{TH}$ here corresponds to the predetermined time $t_B$.

In the normal running mode, which is determined by the mode determiner 21, the failure determining unit 23 accumulates the counter values N of the counter for failure determination to carry out a failure determination. In contrast, in the engine nonoperating mode, which is determined by the mode determiner 21, the failure determining unit 23 puts the counter on hold to suspend the accumulation of the counter values N. In response to the shift from the engine nonoperating mode to the normal running mode (i.e., the termination of the engine nonoperating mode), the failure determining unit 23 restarts the counter for failure determination to resume the failure determination, namely, restart the accumulation from the counter value N immediately before the hold. That is, the failure determination is carried out only in the normal running mode, not in the engine nonoperating mode. This is because a failure in the thermostat 14 in the engine nonoperating mode may be erroneously determined due to the simple calculation of the estimated water temperature $WT_D$ based on the behavior of the actual water temperature WT.

Figure 2A:
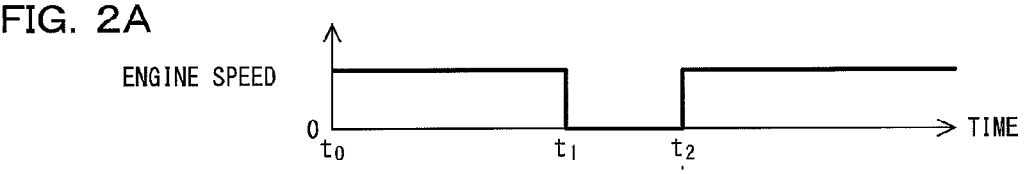
FIGS. 2A to 2D illustrate determination of the normality of the thermostat by the apparatus of determining a failure according to an embodiment.
Figure 2B:
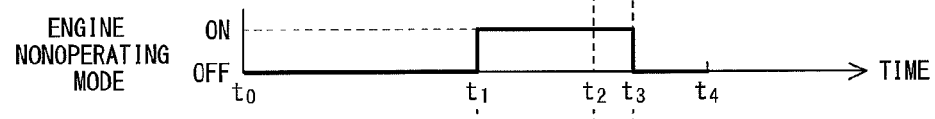
Figure 2C:
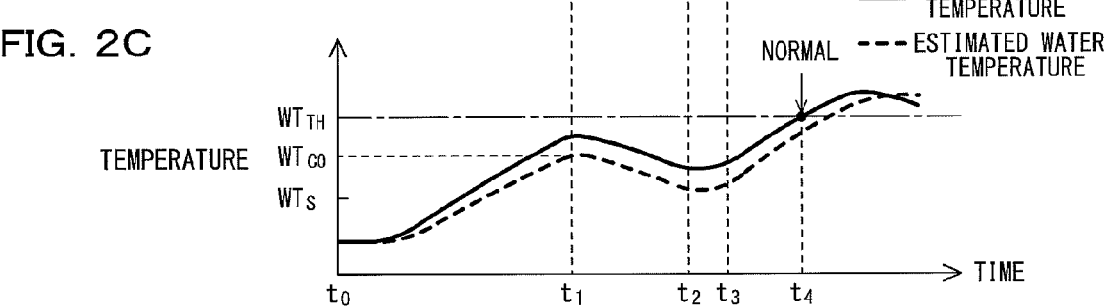
Figure 2D:
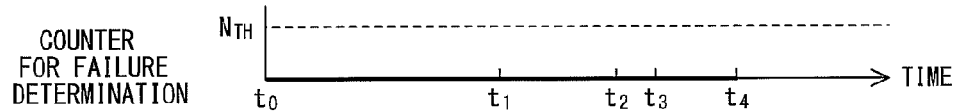
Figure 3A:
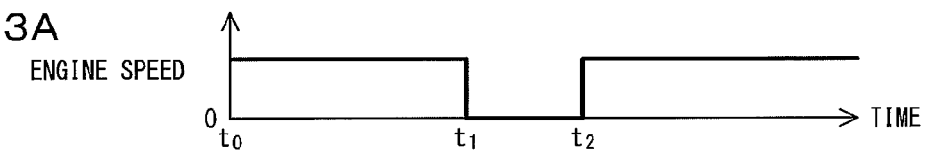
FIGS. 3A to 3D illustrate determination of a failure in the thermostat by the apparatus of determining a failure according to an embodiment.
Figure 3B:
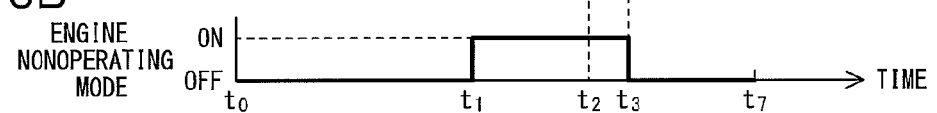
Figure 3C:
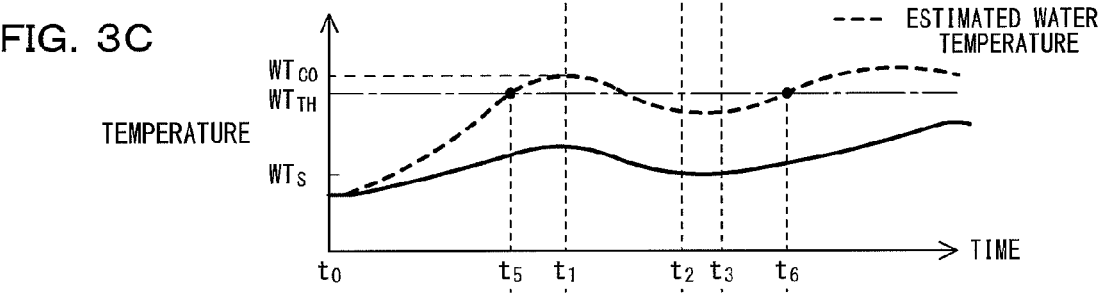
Figure 3D:
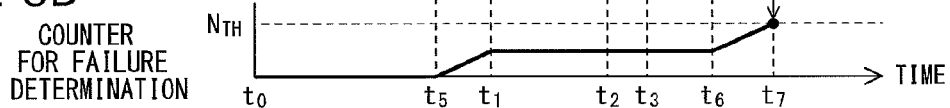

The determination of a failure in the thermostat 14 carried out by the apparatus of a failure determination will now be described with reference to FIGS. 2 and 3. FIGS. 2A and 3A illustrate the engine speed Ne, FIGS. 2B and 3B illustrate an operational mode, FIGS. 2C and 3C illustrate the temperature of a coolant, and FIGS. 2D and 3D illustrate a temporal change in the counter for failure determination. Note that "ON" indicates the engine nonoperating mode, while "OFF" indicates not the engine nonoperating mode (i.e., the normal running mode) in FIGS. 2B and 3B.

With reference to FIGS. 2A, 2B, 3A, and 3B, the engine 10 is automatically stopped at a time $t_1$ and is restarted at a time $t_2$ under the cold start, i.e., in the state where the actual water temperature WT of the coolant at the start $t_0$ of the engine 10 is lower than the start-up determination temperature $WT_S$. The engine speed Ne is zero between the times $t_1$ and $t_2$, and is a predetermined value at the other times. Although FIGS. 2A and 3A indicate the constant engine speed Ne, the engine speed Ne may be any positive number. The vehicle enters the engine nonoperating mode at the time $t_1$, at which the engine speed Ne becomes zero. The engine nonoperating mode continues from the time $t_2$ to a time $t_3$, that is, for the time between the restart of the engine 10 and a lapse of the predetermined time $t_A$. The vehicle enters the normal running mode at the time $t_3$. Note that the vehicle is in the normal running mode also between the times $t_0$ and $t_1$.

The actual water temperature WT of the coolant increases in the normal running mode and gradually decreases in the engine nonoperating mode. Under the normal thermostat 14, the actual water temperature WT is quickly warmed to become equal to or higher than the predetermined temperature $WT_{TH}$ earlier than the estimated water temperature $WT_C$, as illustrated in FIG. 2C. Letting this point of time be $t_4$, the failure determining unit 23 determines the thermostat 14 to be "normal" since condition (4) is fulfilled at the time $t_4$.

In the normal running mode, the estimated water temperature $WT_C$ of the coolant is calculated by the above-described arithmetic method. The estimated water temperature $WT_C$ is slightly lower than the actual water temperature WT, while these temperatures have similar increases. In the engine nonoperating mode, the estimated water temperature $WT_C$ immediately before the shift to the engine nonoperating mode (at the time $t_1$) is supposed to be the starting temperature $WT_{C0}$, and the behavior of the actual water temperature WT is applied to the starting temperature $WT_{C0}$. That is, the estimated water temperature $WT_C$ varies with the same temperature gradient as that of the actual water temperature WT in the engine nonoperating mode between the times $t_1$ and $t_3$.

FIG. 2D illustrates the counter for failure determination. The counter starts to measure time when condition (2) is fulfilled. In FIG. 2D, the counter value N remains constant, i.e., zero, since the thermostat 14 is determined to be normal at the time $t_4$.

In contrast, under the stuck-open thermostat 14, the actual water temperature WT slowly increases due to the circulation of the coolant through the radiator 13; as a result, the estimated water temperature $WT_D$ reaches the predetermined temperature $WT_{TH}$ prior to the actual water temperature WT, as illustrated in FIG. 3C. Letting this point of time be $t_5$, condition (2) is also fulfilled at the time $t_5$ in addition to condition (1); hence, the failure determining unit 23 starts the counter for failure determination. When the vehicle enters the engine nonoperating mode at the time $t_1$ at which the accumulation of counter values N is ongoing, the counter is stopped and holds the counter value N at the time $t_1$.

In the engine nonoperating mode, between the times $t_1$ and $t_3$, the behavior of the actual water temperature WT is applied to the starting water temperature $WT_{C0}$ to calculate an estimated water temperature $WT_C$ in the engine nonoperating mode with the same inclination as that of the actual water temperature WT. At the termination of the engine nonoperating mode, i.e., at the time $t_3$, the counter value N remains constant since the estimated water temperature $WT_C$ is lower than the predetermined temperature $WT_{TH}$. The counter restarts the accumulation from the held counter value N at the time $t_6$ since the estimated water temperature $WT_D$ becomes equal to or higher than the predetermined temperature $WT_{TH}$, that is, conditions (1) and (2) are fulfilled. Continuance of the state of conditions (1) and (2) being fulfilled causes the counter value N to reach the predetermined value $N_{TH}$ at the time $t_7$ and leads to the fulfillment of condition (3); hence, the failure determining unit 23 determines the thermostat 14 to be "valve-open failure."

[3. Flow Charts]

Figure 5:
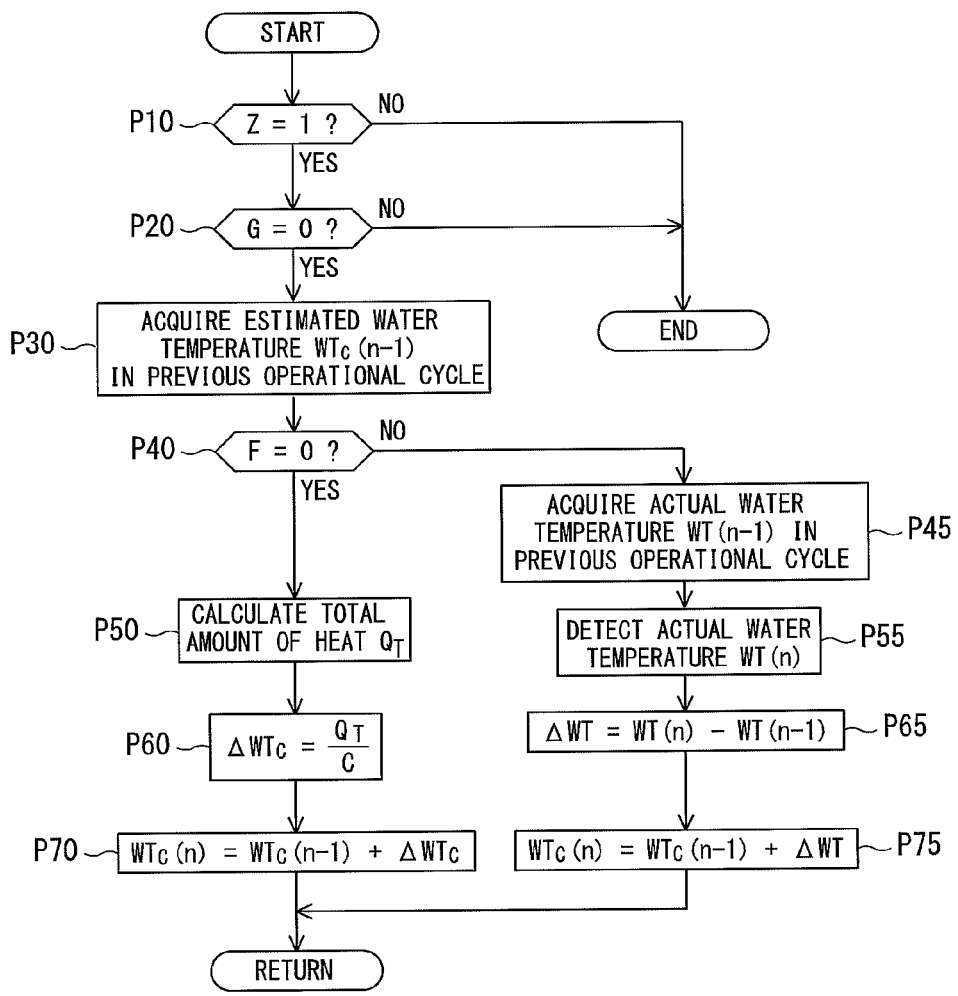
FIG. 5 is a flow chart illustrating a process executed by a water temperature estimator.
Figure 6:
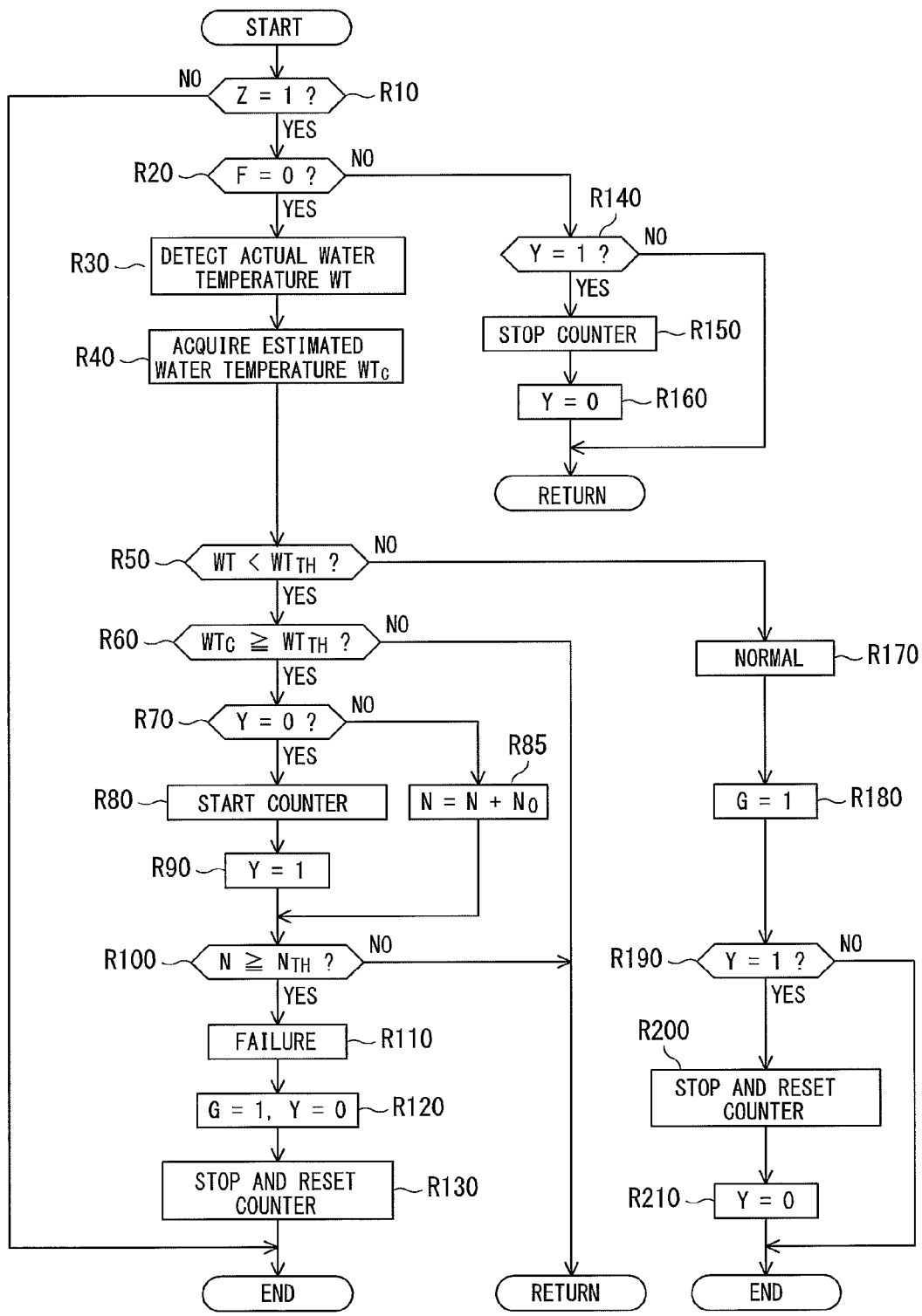
FIG. 6 is a flow chart illustrating a process executed by a failure determining unit.

Exemplary failure determining procedures for the thermostat 14 executed by the vehicle ECU 20 will now be described with reference to FIGS. 4 to 6. FIGS. 4A and 4B are flow charts illustrating processes executed by the mode determiner 21, FIG. 5 is a flow chart illustrating a process executed by the water temperature estimator 22, and FIG. 6 is a flow chart illustrating a process executed by the failure determining unit 23. Each of the flow charts starts when the key is brought to the ON position and repeats itself in a preset predetermined cycle (e.g., a few dozen milliseconds [ms]).

The flow charts of the processes executed by the mode determiner 21 will now be described. With reference to FIG. 4A, the temperature sensor 16 detects the actual water temperature WT in Step M10, and then the mode determiner 21 determines whether the actual water temperature WT is lower than the start-up determination temperature $WT_S$ in Step M20. Step M20 determines whether the engine 10 is cold-started. If the actual water temperature WT is lower than the start-up determination temperature $WT_S$, the process proceeds to Step M30; otherwise, the process proceeds to Step M35. In Step M30, the flag Z is set at 1; whereas in Step M35, the flag Z is set at 0. The flag Z indicates whether the engine 10 is cold-started or hot-started; specifically, "Z=1" corresponds to the cold start, while "Z=0" corresponds to the hot start. Note that Z is set at 0 by default.

If the flag Z is set at 1 in Step M30, the actual water temperature WT detected in Step M10 is stored as an initial actual water temperature WT(0) in Step M40 and then stored as an initial estimated water temperature $WT_C$ (0) in Step M50. The flow then ends. If the flag Z is set at 0 in Step M35, the flow ends. That is, the process of the flow in FIG. 4A is executed only once after the key is brought to the ON position.

With reference to FIG. 4B, Step S10 determines whether the flag Z is 1. If Z=1, the process proceeds to Step S20. If Z=0, the flow ends. That is, the subsequent steps of the flow are executed only under cold start. Step S20 determines whether the flag G is 0. If G=0, the process proceeds to Step S30. If G=1, the process proceeds to Step S22. The flag G indicates whether the failure determining unit 23 has carried out a determination; specifically, "G=0" corresponds to "pre-determination," while "G=1" corresponds to "post-determination." Note that G is set at 0 by default.

In Step S30, the engine speed sensor 17 detects the engine speed Ne. In Step S40, the mode determiner 21 determines whether the engine speed Ne is higher than zero. "Ne>0" indicates that the operational mode is the normal running mode or the engine nonoperating mode within the predetermined time $t_A$ after the restart of the automatically stopped engine 10; hence, Step S50 determines whether the flag F is 1 in order to determine the operational mode, i.e., the normal running mode or the engine nonoperating mode. The flag F indicates whether the operational mode is the normal running mode or the engine nonoperating mode; specifically, "F=0" corresponds to the normal running mode, while "F=1" corresponds to the engine nonoperating mode. Note that F is set at 0 by default.

If the engine speed Ne is determined to be higher than zero in Step S40 and the flag F is determined to be 0 in Step S50, then the mode determiner 21 determines the normal running mode to terminate the control in the current operational cycle with the flag F remaining to be 0. In contrast, if the engine speed Ne is determined to be higher than zero in Step S40 and the flag F is determined to be 1 in Step S50, then the mode determiner 21 determines the engine nonoperating mode within the predetermined time $t_A$ after the restart of the automatically stopped engine 10 to execute Step S60 and the subsequent steps.

If Step S40 determines that the engine speed Ne is not higher than zero (i.e., Ne=0), Step S45 determines whether the key is in the ON position. If the engine speed Ne is zero and the key is in the ON position, the mode determiner 21 determines the engine nonoperating mode. The process then proceeds to Step S105 to set the flag F at 1, and then terminates the control in the current operational cycle.

Also in the subsequent operational cycles, if the flag G is 0 and the engine speed Ne is zero as well as the key is in the ON position, then the flag F is set at 1 in Step S105 each time. The restart of the engine 10 causes the engine speed Ne to be higher than zero; hence, the process proceeds to Step S50 to determine the flag F. Now the flag F is 1, so that the process proceeds to Step S60.

Step S60 determines whether the flag X is 0. The flag X is a variable for determining the measurement state of a timer A; specifically, "X=0" corresponds to the timer A stopped, while "X=1" corresponds to the timer A measuring time. Note that X is set at 0 by default. The timer A measures time elapsed from the restart of the engine 10. That is, the condition of "Ne>0," "F=1," and "X=0" corresponds to the time $t_2$ in FIGS. 2 and 3; hence, Step S70 starts the timer A to measure the predetermined time $t_A$. Thereafter, Step S80 sets the flag X at 1, and then Step S90 determines whether the time measured by the timer A is equal to or longer than the predetermined time $t_A$. If the predetermined time $t_A$ has not elapsed from the start of the measurement by the timer A (i.e., at the time $t_2$ in FIGS. 2 and 3), then the control in the current operational cycle is terminated.

In the next operational cycle, the condition of "G=0" and "Ne>0" leads to the determination of the flag F in Step S50, followed by the determination of the flag X in Step S60. Since the timer A has already started measurement in this operational cycle, the process proceeds to Step S90 through the NO route and the flow is repeated. If the timer A is determined to be equal to or higher than the predetermined time $t_A$ in Step S90, the flag F is set at 0 in Step S100. In Step S110, the timer A is stopped and reset. In Step S120, the flag X is reset to 0. The control in this operational cycle is then terminated. That is, the operational mode shifts to the normal running mode after a lapse of the predetermined time $t_A$ from the restart of the engine 10.

After the determination of the flag G being 1 in Step S20, the process proceeds to Steps S22, S24, and S26, where the flags Z, F, and G are all reset to 0, and then the process ends. That is, the process of the flow chart is repeated until the execution of a determination by the failure determining unit 23 (the flag G being set at 1) or the key being brought to the OFF position.

The flow chart of the process executed by the water temperature estimator 22 will now be described. With reference to FIG. 5, Step P10 determines whether the flag Z is 1. If Z=1, the process proceeds to Step P20; otherwise, the flow ends. Step P20 determines whether the flag G is 0. If G=1, the flow ends. That is, the process of the flow is executed only under cold start and before a determination by the failure determining unit 23.

If G=0, the process proceeds to Step P30 to acquire the estimated water temperature $WT_C$ (n−1), which has been calculated in the previous operational cycle. In the flow chart of FIG. 5, the current operational cycle is denoted by (n), while the previous operational cycle is denoted by (n−1). Note that the initial values determined in Steps M40 and M50 in FIG. 4A are used in the first operational cycle (i.e., n=1).

Step P40 determines whether the flag F is 0. If F=0 (normal running mode), the process proceeds to Step P50. Step P50 calculates the total amount of heat $Q_T$, Step P60 calculates the variation in water temperature $\Delta WT_C$, and Step P70 adds the variation in water temperature $\Delta WT_C$ calculated in Step P60 to the estimated water temperature $WT_C(n-1)$ acquired in Step P30 to calculate the estimated water temperature $WT_C(n)$ in the current operational cycle. The control in this operational cycle is then terminated.

In contrast, if F=1 (engine nonoperating mode), the process proceeds to Step P45 to acquire the actual water temperature WT(n−1) in the previous operational cycle. Step P55 detects the actual water temperature WT(n) in the current operational cycle, and Step P65 calculates the variation $\Delta WT$ in the actual water temperature WT. Step P75 adds the variation $\Delta WT$ in the actual water temperature calculated in Step P65 to the estimated water temperature $WT_D$ (n−1) acquired in Step P30 to calculate the estimated water temperature $WT_C(n)$ in the current operational cycle, and the control in this operational cycle is then terminated. That is, the estimated water temperature $WT_C$ in the engine nonoperating mode is calculated by the addition of the variation $\Delta WT$ in the actual water temperature WT.

Finally, the flow chart of the process executed by the failure determining unit 23 will now be described. With reference to FIG. 6, Step R10 determines whether the flag Z is 1. If Z=1, the process proceeds to Step R20; otherwise, the flow ends. That is, the process of the flow is executed only under cold start. Step R20 determines whether the flag F is 0. If F=0, the process proceeds to Step R30; otherwise, the process proceeds to Step R140.

In the normal running mode (F=0), Step R30 detects the actual water temperature WT, and Step R40 acquires an estimated water temperature $WT_C$. Step R50 determines whether the actual water temperature WT is lower than the predetermined temperature $WT_{TH}$. If the actual water temperature WT is lower than the predetermined temperature $WT_{TH}$, the process proceeds to Step R60 to determine whether the estimated water temperature $WT_C$ is equal to or higher than the predetermined temperature $WT_{TH}$. If the estimated water temperature $WT_C$ is lower than the predetermined temperature $WT_{TH}$, the control in this operational cycle is then terminated. In contrast, if the actual water temperature WT is lower than the predetermined temperature $WT_{TH}$ and the estimated water temperature $WT_C$ is equal to or higher than the predetermined temperature $WT_{TH}$, the thermostat 14 may be valve-open failure; hence, the counter for failure determination is started for the execution of a failure determination. First, Step R70 determines whether the flag Y is 0. Note that the flag Y is a variable used for determining the operational state of counter. Specifically, "Y=0" corresponds to the counter stopped, while "Y=1" corresponds to the counter operating. Note that Y is set at 0 by default.

If the counter for failure determination is stopped, Step R80 starts the counter, and then Step R90 sets the flag Y at 1. Then, Step R100 determines whether the counter value N is equal to or higher than the predetermined value $N_{TH}$. If the counter value N is lower than the predetermined value $N_{TH}$, the control in this operational cycle is then terminated. In the next cycle, since the flag Y is 1, the process proceeds from Step R70 to Step R85 through the NO route to accumulate the counter values N. Note that the value $N_0$ added to the previous counter value N in Step R85 is determined depending on the predetermined cycle for the flow and the predetermined value $N_{TH}$ (predetermined time $t_B$).

If Step R100 determines the accumulated counter value N to be equal to or higher than the predetermined value $N_{TH}$, the process proceeds to Step R110 to determine a "valve-open failure" in the thermostat 14. Step R120 sets the flag G at 1 and the flag Y at 0. Step R130 stops and resets the counter, and then the flow ends.

If Step R50 determines the actual water temperature WT to be equal to or higher than the predetermined temperature $WT_{TH}$, the process proceeds to Step R170 to determine the thermostat 14 to be "normal." That is, if the actual water temperature WT reaches the predetermined temperature $WT_{TH}$ before the determination of a failure in the thermostat 14, Step R170 determines the normality and then Step R180 sets the flag G at 1. If the counter for failure determination is operating (Y=1) at this time, the process proceeds from Step R190 to Step R200 through the YES route to stop and reset the counter. Step R210 resets the flag Y to 0, and then the flow ends. If the counter is stopped (Y=0), then the flow ends.

In the engine nonoperating mode (F=1), the process proceeds from Step R20 to Step R140 to determine whether the flag Y is 1, i.e., whether the counter for failure determination is operating. If the counter is operating (Y=1), Step R150 stops the counter, and the counter value N at this time is held. Step R160 sets the flag Y at 0, and then the control in this operational cycle is terminated. If Step R140 determines that the counter is stopped (Y=0), then the control in this operational cycle is terminated.

[4. Advantages]

In summary, the apparatus of determining a valve-open failure in the thermostat 14 according to the present embodiment compares the actual water temperature WT with the estimated water temperature $WT_C$. In the engine nonoperating mode including at least automatic stop of the engine 10, the apparatus applies the behavior of the actual water temperature WT to the estimated water temperature $WT_C$ calculated immediately before the automatic stop of the engine 10 to calculate the estimated water temperature $WT_C$ in the engine nonoperating mode. This can prevent a reduction in estimation accuracy of the estimated water temperature $WT_C$ during the automatic stop of the engine 10.

That is, in the engine nonoperating mode, the estimated water temperature $WT_C$ determined from the behavior of the actual water temperature WT does not involve a significant deviation from the actual variation in the coolant (i.e., change in the actual water temperature WT), which can ensure the accuracy of estimating the temperature of the coolant even during the automatic stop of the engine 10. Accordingly, a failure in the thermostat 14 can be determined using the high-accuracy estimated water temperature $WT_C$, which can lead to an improvement in the accuracy of the failure determination. In addition, an operation load can be suppressed with the simple configuration that only applies the behavior of the actual water temperature WT to the estimated water temperature $WT_C$ calculated immediately before the automatic stop.

Furthermore, in the engine nonoperating mode, the water temperature estimator 22 calculates the estimated water temperature $WT_C$ with the same temperature gradient as that of the actual water temperature WT, which can ensure the accuracy of estimating the temperature of the coolant with a simplified configuration.

Moreover, the mode determiner 21 in the present embodiment determines the engine nonoperating mode not only during the automatic stop of the engine 10 but also within the period from the restart of the automatically stopped engine 10 to a lapse of the predetermined time $t_A$, which can ensure the accuracy of estimating the temperature of the coolant and the accuracy of the failure determination.

Additionally, the failure determining unit 23 stops the comparison between the actual water temperature WT and the estimated water temperature $WT_C$ in the engine nonoperating mode and restarts the comparison at the termination of the engine nonoperating mode, which can reliably prevent an erroneous determination of the operational condition. That is, an erroneous determination due to the simple calculation of the estimated water temperature $WT_C$ can be prevented by stopping the failure determination during the engine nonoperating mode.

[5. Modifications]

The above-described embodiment of the present invention should not be construed to limit the present invention and may be modified in various manners without deviation from the gist of the present invention.

In the above-described embodiment, the time period of the engine nonoperating mode determined by the mode determiner 21 is from the automatic stop of the engine 10 to a lapse of the predetermined time $t_A$ after the restart of the engine 10, and the predetermined time $t_A$ is a predefined constant value. The engine nonoperating mode, however, is not limited to this condition.

For example, the predetermined time $t_A$ may be varied depending on the variation $\Delta WT$ in the actual water temperature WT during the automatic stop of the engine 10. That is, the mode determiner 21 preliminarily stores a referential predetermined time $t_A$. If the variation $\Delta WT$ in the actual water temperature WT calculated by the water temperature estimator 22 during the automatic stop of the engine 10 is large, then the mode determiner 21 prolongs the predetermined time $t_A$. In contrast, if the variation $\Delta WT$ in the actual water temperature WT is small, the mode determiner 21 shortens the predetermined time $t_A$. In other words, in the case of a large variation $\Delta WT$ in the actual water temperature WT, a longer wait time (predetermined time $t_A$) is assumed to level out the uneven temperatures of the coolant after the restart of the engine 10; hence, the predetermined time $t_A$ is prolonged. In contrast, in the case of a small variation $\Delta WT$ in the actual water temperature WT, the uneven temperatures are assumed to be leveled out relatively early; hence the predetermined time $t_A$ is shortened. As a result, the engine nonoperating mode can be properly determined.

Note that the referential predetermined time may or may not be the same as the predetermined time $t_A$ described in the above embodiment. Furthermore, the predetermined time may be varied depending on the time period of the engine 10 being automatically stopped (automatic stop time), instead of the variation $\Delta WT$ in the actual water temperature WT in the automatically stopped engine 10. This is because a longer automatic stop time increases the variation $\Delta WT$ in the actual water temperature WT and a shorter automatic stop time reduces the variation $\Delta WT$ in the actual water temperature WT, that is, the variation $\Delta WT$ in the actual water temperature WT in the automatically stopped engine 10 is correlative to the stop time.

The mode determiner 21 may also determine the engine nonoperating mode during only the automatic stop of the engine 10. That is, the engine nonoperating mode may exclude the predetermined time $t_A$ after the restart of the engine 10. Consequently, monitoring only the engine speed Ne of the engine 10 can lead to the determination of the engine nonoperating mode, i.e., simpler control is achieved.

Furthermore, if a failure determination for the thermostat 14 is stopped in the engine nonoperating mode, the water temperature estimator 22 may calculate the estimated water temperature $WT_C$ only at the termination of the engine nonoperating mode. That is, the estimated water temperature $WT_C$ at the termination of the engine nonoperating mode (time $t_3$) may be calculated by the addition of the variation $\Delta WT_{3-1}$ ($\Delta WT_{3-1} < 0$) in the actual water temperature WT during the engine nonoperating mode (times $t_1$ to $t_3$ in FIGS. 2 and 3) to the estimated water temperature $WT_C$ (starting temperature $WT_{C0}$) calculated immediately before the engine nonoperating mode, without monitoring the estimated water temperature $WT_C$ during the engine nonoperating mode. Accordingly, the estimated water temperature $WT_C$ can be more readily calculated.

Note that the failure determination may also continue during the engine nonoperating mode. In this case, the behavior of the actual water temperature WT acquired by continuous monitoring may be applied to the calculation of the estimated water temperature $WT_C$.

Alternatively, the failure determining unit 23 may determine the fulfillment of condition (3) when the timer started at the time of the fulfillment of condition (2) indicates a lapse of the predetermined time $t_B$. Furthermore, a valve-open failure in the thermostat 14 may be determined by the failure determining unit 23 on the basis of other conditions than conditions (1) to (3). For example, the predetermined temperature $WT_{TH}$ may also be different between conditions (1) and (2), and condition (3) may not be necessary.

Moreover, the above-described flowcharts and methods of calculating the estimated water temperature $WT_C$ in the normal running mode are only examples, and any other method and flow chart may also be adopted.

Furthermore, the apparatus of determining a failure in a thermostat can be applied to any of various vehicles equipped with engines.

REFERENCE SIGNS LIST 10 engine
11 cooling channel
12 water pump
13 radiator
14 thermostat
15 heater
16 temperature sensor (water temperature detector)
17 engine speed sensor
18 vehicle speed sensor
20 vehicle ECU
21 mode determiner
22 water temperature estimator
23 failure determining unit
WT actual water temperature
$WT_C$ estimated water temperature The invention thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus of determining a failure in a thermostat for controlling the flow of a coolant into a radiator in response to an actual water temperature of the coolant for an engine in a vehicle, the apparatus comprising:
   a water temperature detector that detects the actual water temperature; and
   a controller including:
      a water temperature estimator that calculates an estimated water temperature of the coolant; and
      a failure determining unit that compares the actual water temperature detected by the water temperature detector with the estimated water temperature calculated by the water temperature estimator under cold start of the engine and determines whether the thermostat is valve-open failure,
   wherein in an automatic stop state of the engine, the water temperature estimator applies a behavior of the actual water temperature to an estimated water temperature calculated immediately before automatic stop of the engine to calculate, based on a temperature gradient of the actual water temperature such that a temperature gradient of an estimated water temperature in the automatic stop state of the engine varies identical to the temperature gradient of the actual water temperature, the estimated water temperature in the automatic stop state of the engine.

2. The apparatus of determining a failure in the thermostat according to claim 1, further comprising:
   an engine speed sensor that detects an engine speed of the engine,
   the controller further includes:
   a mode determiner that determines whether the vehicle is in the automatic stop state as an engine nonoperating mode based on the detected actual water temperature and the detected engine speed,
   wherein the mode determiner also determines that a period from a restart of the automatically stopped engine until a lapse of a predetermined time to be included in the engine nonoperating mode.

3. The apparatus of determining a failure in the thermostat according to claim 2, wherein
   the mode determiner revises the predetermined time in response to a variation in the actual water temperature in the automatically stopped engine.

4. The apparatus of determining a failure in the thermostat according to claim 3, wherein
   the failure determining unit stops comparison between the actual water temperature and the estimated water temperature in the engine nonoperating mode and restarts the comparison at the termination of the engine nonoperating mode.

5. The apparatus of determining a failure in the thermostat according to claim 4, wherein
   at the termination of the engine nonoperating mode, the water temperature estimator adds a variation in the actual water temperature during a period between a time immediately before the automatic stop and the termination to the estimated water temperature calculated immediately before the automatic stop.

6. The apparatus of determining a failure in the thermostat according to claim 2, wherein
   the failure determining unit stops comparison between the actual water temperature and the estimated water temperature in the engine nonoperating mode and restarts the comparison at the termination of the engine nonoperating mode.

7. The apparatus of determining a failure in the thermostat according to claim 6, wherein
   at the termination of the engine nonoperating mode, the water temperature estimator adds a variation in the actual water temperature during a period between a time immediately before the automatic stop and the termination to the estimated water temperature calculated immediately before the automatic stop.

8. The apparatus of determining a failure in the thermostat according to claim 1, wherein
   the failure determining unit stops comparison between the actual water temperature and the estimated water temperature in the engine nonoperating mode and restarts the comparison at the termination of the engine nonoperating mode.

9. The apparatus of determining a failure in the thermostat according to claim 8, wherein
   at the termination of the automatic stop state of the engine, the water temperature estimator adds a variation in the actual water temperature during a period between a time immediately before the automatic stop and the termination to the estimated water temperature calculated immediately before the automatic stop.

10. A method of determining a failure in a thermostat for controlling the flow of a coolant into a radiator in response to an actual water temperature of the coolant for an engine in a vehicle, the method comprising:
    determining whether the engine is cold-started;
    detecting the actual water temperature, if the engine is cold-started, and applying a behavior of the actual water temperature to an estimated water temperature calculated immediately before automatic stop of the engine in an engine automatic stop state of the engine to calculate, based on a temperature gradient of the actual water temperature such that a temperature gradient of an estimated water temperature varies in the automatic stop state of the engine varies identical to the temperature gradient of the actual water temperature, the estimated water temperature in the automatic stop state of the engine; and
    comparing the actual water temperature with the estimated water temperature to determine whether the thermostat is valve-open failure.

* * * * *